(12) United States Patent
Miller-Larry

(10) Patent No.: US 8,197,761 B1
(45) Date of Patent: Jun. 12, 2012

(54) VEHICLE AIR FRESHENER

(76) Inventor: Shelia Miller-Larry, Glenn Heights, TX (US)

(*) Notice: Subject to any disclaimer, the term of this patent is extended or adjusted under 35 U.S.C. 154(b) by 440 days.

(21) Appl. No.: 12/537,539

(22) Filed: Aug. 7, 2009

Related U.S. Application Data

(60) Provisional application No. 61/087,261, filed on Aug. 8, 2008.

(51) Int. Cl.
*A62B 7/08* (2006.01)
*A61M 16/00* (2006.01)
*F24F 3/14* (2006.01)
*F24F 6/00* (2006.01)

(52) U.S. Cl. .................. 422/125; 392/390; 392/391

(58) Field of Classification Search .......... 392/390–391; 422/125

See application file for complete search history.

(56) References Cited

U.S. PATENT DOCUMENTS

| | | | |
|---|---|---|---|
| 4,808,347 A | 2/1989 | Dawn | |
| 5,394,506 A | 2/1995 | Stein et al. | |
| 5,432,882 A | 7/1995 | Glynn | |
| 6,021,254 A | 2/2000 | Hunter | |
| 6,197,263 B1 | 3/2001 | Blount | |
| 2005/0175513 A1* | 8/2005 | Hart et al. | 422/125 |

* cited by examiner

*Primary Examiner* — Walter D Griffin
*Assistant Examiner* — Christopher Vandeusen
(74) *Attorney, Agent, or Firm* — Kenneth L Tolar

(57) ABSTRACT

A vehicle air freshener includes an elongated, substantially cylindrical housing having an angled upper end, a lower end and an interior chamber. Within the interior chamber is an electric heater and a removable cartridge containing a fragrant or deodorizing material. The heater is powered by a conventional adapter on the lower end of the housing that mates with the vehicle's cigarette lighter. At the upper end of the housing is an adjustable fan assembly for dispersing the fragrant material into the vehicle passenger compartment. Accordingly, the adapter is properly inserted into the vehicle's cigarette lighter and a switch is engaged to activate the fan and heater; the fragrant material within the cartridge is slowly vaporized and dispersed to the atmosphere.

7 Claims, 2 Drawing Sheets

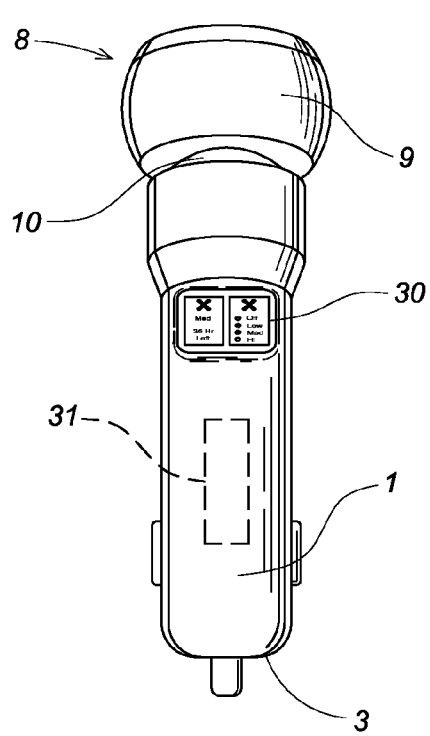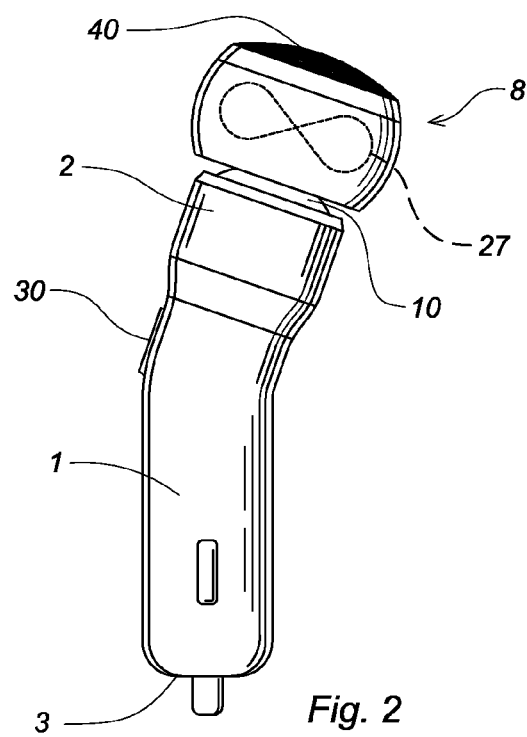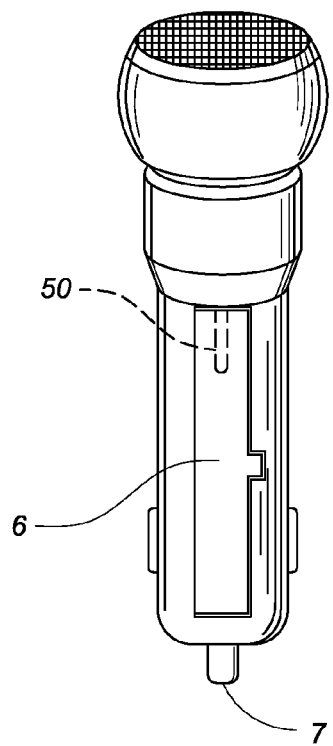
Fig. 1
Fig. 2
Fig. 3

VEHICLE AIR FRESHENER

CROSS REFERENCE TO RELATED APPLICATIONS

This application is entitled to the benefit of provisional application No. 61/087,261 filed on Aug. 8, 2008, the specification of which is incorporated herein by reference.

BACKGROUND OF THE INVENTION

The present invention relates to a vehicle air freshener.

DESCRIPTION OF THE PRIOR ART

A myriad of vehicle deodorizers exist in the prior art for removing or masking undesirable odors within the passenger compartment. Most are either spray dispensers, or sheets saturated with a scented material that are suspended within the passenger compartment. However, spray dispensers are initially overwhelming and then dissipate rapidly while the saturated sheets are obstructive and unsightly. Accordingly, there is currently a need for an unobtrusive vehicle air freshener that gradually and continuously disperses scented material into a passenger compartment.

A review of the prior art reveals a myriad of automated air fresheners for a vehicle, which are purported to address this problem. For example, U.S. Pat. No. 4,808,347 issued to Dawn discloses a vehicle air freshener including a housing having a plug for mating engagement with a vehicle cigarette lighter. Within the housing is an electric fan that disperses a scented material through a perforated, dome-shaped cover and into the vehicle passenger compartment.

U.S. Pat. No. 6,197,263 issued to Blount discloses a vehicle air freshener comprising a fragrance-dispensing unit having a power cord with a cigarette lighter adapter attached thereto. The fragrance dispensing unit includes a heater and an associated scented cartridge. The unit is attachable to an air vent so that the vehicle's air conditioning system distributes the generated fragrance throughout the passenger compartment.

U.S. Pat. No. 6,021,254 issued to Hunter discloses a vehicle air freshener having a heater that is activated by a timer to vaporize and deliver a scented material to a vehicle passenger compartment.

U.S. Pat. No. 5,394,506 issued to Stein et al. discloses a fragrance dispenser for an automobile including a housing having a cigarette lighter adapter that powers a heater. A wedge-shaped, scented cartridge is housed within a similarly-shaped, perforated compartment from which a scented material is released to the atmosphere.

U.S. Pat. No. 5,432,882 issued to Glynn discloses a vehicle deodorizer having a controller that activates a heating element only if a minimum quantity of scented material is present.

As indicated above, several powered fragrance dispensers for vehicles exist in the prior art. However, none of the conventional dispensers are angularly adjustable to dispense a scented material in a desired direction. Furthermore, none of the devices visually depict the remaining amount of the scented material. Conversely, the present invention provides an air freshener that is powered by the vehicle's cigarette lighter having an angularly adjustable fan assembly for dispersing scented material in a desired direction. A microprocessor monitors dispersal rates and durations to calculate a remaining inventory, which is continuously depicted on a display.

SUMMARY OF THE INVENTION

The present invention relates to a vehicle air freshener comprising an elongated, substantially cylindrical housing having an angled upper end, a lower end and an interior chamber. Within the interior chamber is an electric heater and a removable cartridge containing a fragrant or deodorizing material. The heater is powered by a conventional adapter on the lower end of the housing that is coupled with the vehicle's cigarette lighter. At the upper end of the housing is an angularly-adjustable fan assembly for dispersing vaporized scented material into the vehicle passenger compartment. Accordingly, the adapter is properly inserted into the vehicle's cigarette lighter and a switch is engaged to activate the fan and heater; the fragrant material within the cartridge is slowly vaporized and dispersed to the atmosphere.

It is therefore an object of the present invention to provide a device that overcomes the deficiencies associated with conventional vehicle air fresheners.

It is another object of the present invention to provide a vehicle air freshener that includes a heater and a fan for continuously dispersing scented material into a vehicle passenger compartment.

Other objects, features, and advantages of the present invention will become readily apparent from the following detailed description of the preferred embodiment when considered with the attached drawings and the appended claims.

BRIEF DESCRIPTION OF THE DRAWINGS

FIG. 1 is a front, plan view of the air freshener according to the present invention.

FIG. 2 is a side view of the air freshener.

FIG. 3 is a rear view of the air freshener.

DESCRIPTION OF THE PREFERRED EMBODIMENT

Figure 5:
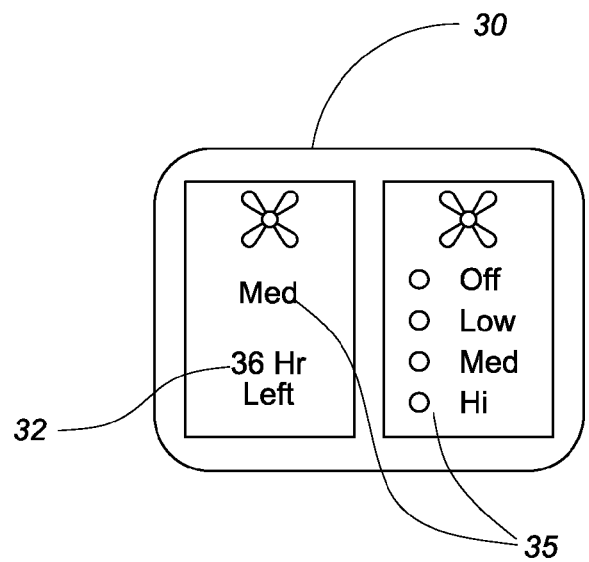
FIG. 5 is an isolated view of the display.
Figure 4:
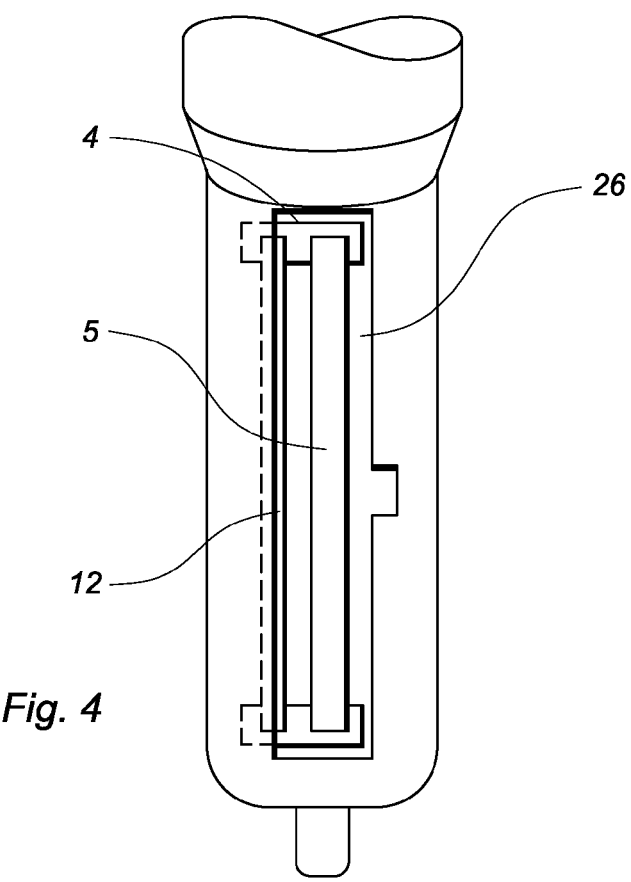
FIG. 4 is a rear view of the air freshener with the door in an open position to expose the support rack.

The present invention relates to a vehicle air freshener comprising an elongated, substantially cylindrical housing 1 having an obliquely-extending upper end 2, a lower end 3 and an interior chamber 26. Within the chamber is a rack 4 that supports an electrical heater 12 and a removable cartridge 5 containing a fragrant or deodorizing material. A pivotal door 6 provides selective access to the rack allowing the cartridge to be removed and replaced. The heater is powered by a conventional adapter 7 on the lower end of the housing that mates with the vehicle's cigarette lighter.

At the upper end of the housing is a fan assembly 8 including a vented casing 9 in fluid communication with the cartridge and an internally-disposed, DC-operated fan 27. The casing is mounted on a semispherical ball 10 that allows the vents to be reoriented as desired. Preferably, the casing also includes an opening 40 formed into a predetermined pattern, such as a logo, that is illuminated by an internal LED when the fan is operating.

On the exterior surface of the housing is a touch screen display 30 in communication with an internally-disposed microprocessor 31. A switch 50 positioned on the door 6 communicates with the microprocessor to initiate an inventory-monitoring procedure. Whenever the door is opened and subsequently closed, the microprocessor assumes that the cartridge is full and applies an algorithm that monitors fan speed and operational duration to estimate actual usage. The estimated usage is deducted from an original, predefined full-cartridge volume to calculate a remaining inventory 32 in hours, which is subsequently depicted on the display.

The touch screen display further includes a plurality of icons 35 that allow a user to preselect a fan speed. For example, HIGH, MED and LOW icons may be engaged to activate the heater and the fan at the desired speed.

Accordingly, the adapter is properly inserted into the vehicle's cigarette lighter and the appropriate icon on the touchscreen display is engaged to activate the fan and heater; the fragrant material within the cartridge is slowly vaporized and dispersed to the atmosphere. A vehicle passenger can easily reposition the vents by rotating the housing within the cigarette lighter to reorient the angled upper end. The vents are further adjustable by swivelling the casing to a desired orientation relative to the housing. The remaining life of the cartridge is continuously depicted on the display allowing a user to anticipate when the cartridge must be replaced.

The above-described device is not limited to the exact details of construction and enumeration of parts provided herein. Furthermore, the size, shape and materials of construction of the various components can be varied.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A vehicle air freshener comprising:
   an elongated housing having an obliquely-extending upper end, a lower end and an interior chamber;
   a cartridge received within said interior chamber, said cartridge containing a scented material;
   a heater proximal said cartridge for vaporizing said scented material;
   a fan assembly in fluid communication with said cartridge and pivotally mounted on the upper end of said housing for dispersing said scented material in a desired direction;
   wherein said fan assembly comprises:
   a vented casing having an electrical fan disposed therein;
   wherein said casing is mounted on a semispherical ball that allows the casing to be reoriented relative to said housing.

2. The vehicle air freshener according to claim 1 further comprising a pivotal door on said housing that provides selective access to said cartridge.

3. The vehicle air freshener according to claim 1 further comprising means for monitoring and displaying a remaining inventory of scented material within said cartridge.

4. The vehicle air freshener according to claim 3 wherein said means for monitoring and displaying a remaining inventory of scented material within said cartridge comprises:
   a microprocessor having an algorithm capable of monitoring a speed and operational duration of said fan;
   a switch positioned on said door in communication with said microprocessor, said switch actuating said algorithm when said door is opened and subsequently closed whereby said algorithm calculates actual usage each time said fan is activated and subtracts said actual usage from an initial predefined inventory to calculate a remaining inventory;
   a display on said housing and in communication with said microprocessor for depicting said remaining inventory.

5. The vehicle air freshener according to claim 4 further comprising a plug on said housing adapted to mate with a vehicle's cigarette lighter to power said heater, display and fan.

6. The vehicle air freshener according to claim 5 wherein said casing includes an opening formed into a predetermined design element that is illuminated by an internal LED when the fan is operating.

7. The vehicle air freshener according to claim 6 wherein said display includes a touch screen having a plurality of functional icons thereon that allow a user to preselect a fan speed.

* * * * *